US009890349B2

(12) United States Patent
Rautiainen et al.

(10) Patent No.: US 9,890,349 B2
(45) Date of Patent: Feb. 13, 2018

(54) PROCESS AND SYSTEM FOR PRODUCING LIQUID BIOFUEL FROM BIO-BASED OILS AND/OR FATS

(71) Applicant: BioGTS Oy, Jyvaskyla (FI)

(72) Inventors: Mika Rautiainen, Leppavesi (FI); Annimari Lehtomaki, Petajavesi (FI)

(73) Assignee: BioGTS, Jyvaskyla (FI)

( * ) Notice: Subject to any disclaimer, the term of this patent is extended or adjusted under 35 U.S.C. 154(b) by 0 days.

(21) Appl. No.: 15/171,356

(22) Filed: Jun. 2, 2016

(65) Prior Publication Data
US 2016/0281029 A1    Sep. 29, 2016

Related U.S. Application Data

(63) Continuation-in-part of application No. PCT/FI2014/050981, filed on Dec. 10, 2014.

(30) Foreign Application Priority Data

Dec. 11, 2013 (FI) ...................................... 20136242

(51) Int. Cl.
  *C11C 3/00* (2006.01)
  *C07C 67/02* (2006.01)
  (Continued)

(52) U.S. Cl.
  CPC .............. *C11C 3/003* (2013.01); *C07C 67/02* (2013.01); *C10L 1/026* (2013.01); *C10L 1/19* (2013.01);
  (Continued)

(58) Field of Classification Search
  CPC .................................. C11C 3/003; C10L 1/19
  See application file for complete search history.

(56) References Cited

U.S. PATENT DOCUMENTS 6,887,283 B1    5/2005  Ginosar et al.
2007/0214712 A1    9/2007  Garwood
(Continued)

FOREIGN PATENT DOCUMENTS

EP         1126011        8/2001
WO      2007/142983      12/2007

OTHER PUBLICATIONS

Bernal, J.M. et al., Supercritical synthesis of biodiesel, 2012, Molecules, vol. 17, No. 12, pp. 8696-8719 (Year: 2012).*
(Continued)

*Primary Examiner* — Yate' K Cutliff
(74) *Attorney, Agent, or Firm* — Fildes & Outland, P.C.

(57) ABSTRACT

A process for utilizing bio-based oils and/or fats for producing biofuels includes the steps of: mixing alcohol with a raw material for forming a reaction mixture; pumping the reaction mixture to a reactor; mixing biogas as a catalyst with the reaction mixture in a selected process step either before or after the supply of the reaction mixture to a high-pressure pump, the biogas including methane and carbon dioxide; adjusting a temperature and pressure of the reactor so that the reaction mixture achieves a supercritical state; esterifying the reaction mixture to produce liquid biofuel and by-products; separating the by-products including methane and alcohol from the liquid biofuel; and recovering separated methane. An equivalent system for utilizing bio-based oils and/or fats for producing biofuels is also disclosed.

22 Claims, 5 Drawing Sheets

(51) Int. Cl.
    *C10L 1/19*    (2006.01)
    *C10L 1/02*    (2006.01)
    *C11B 13/00*   (2006.01)
    *C07C 67/00*   (2006.01)

(52) U.S. Cl.
    CPC .............. *C11B 13/00* (2013.01); *C07C 67/00* (2013.01); *C10L 2200/0476* (2013.01); *C10L 2270/026* (2013.01); *C10L 2290/06* (2013.01); *C10L 2290/24* (2013.01); *C10L 2290/46* (2013.01); *C10L 2290/543* (2013.01); *Y02E 50/13* (2013.01); *Y02P 30/20* (2015.11); *Y02W 30/74* (2015.05)

(56) References Cited

U.S. PATENT DOCUMENTS

2008/0221344 A1    9/2008    Gleason et al.
2012/0079760 A1    4/2012    Savage et al.

OTHER PUBLICATIONS

Search Report, Finnish Application No. 20136242, dated Aug. 14, 2014.
International Search Report, International Application No. PCT/FI2014/050981, dated Apr. 1, 2015.
Han H et al., Preparation of biodiesel from soybean oil using supercritical methanol and $CO_2$ as co-solvent, Process Biochemistry, Sep. 1, 2005, vol. 40, nr 9, p. 3148-3151.

* cited by examiner

PROCESS AND SYSTEM FOR PRODUCING LIQUID BIOFUEL FROM BIO-BASED OILS AND/OR FATS

CROSS-REFERENCE TO RELATED APPLICATIONS

This application is a continuation-in-part of International Patent Application No. PCT/FI2014/050981 filed Dec. 10, 2014, which claims the benefit of Finnish Patent Application No. 20136242 filed Dec. 11, 2013, both of which are incorporated by reference in their entirety.

FIELD OF THE INVENTION

The invention relate to a process and system for utilizing bio-based oils and/or fats for producing biofuels using a high pressure reactor. The invention also relates to biofuel production, particularly biodiesel production. Biodiesel is a renewable fuel corresponding to diesel oil, produced from bio-based fats and oils. Biodiesel production is based on a chemical esterification process, wherein biodiesel is produced by esterification from bio-based fats and oils in the presence of alcohol as well as an acid or a base, for example.

BACKGROUND OF THE INVENTION

A biodiesel manufacturing process by esterification using bio-based raw materials is known as prior art. More precisely, the manufacturing process is transesterification, wherein triglyceride is converted to ester. When manufacturing biodiesel from vegetable oils, triglycerides react with alcohol to form glycerol and alkyl esters, such as methyl esters, of fatty acids. In the manufacturing process, triglyceride is gradually converted to diglyceride, monoglyeride and finally, to glycerol. Regarding esterification, water contained in the raw material is detrimental, because together with the base, which is used as catalyst, and fats, it forms soap instead of biodiesel. Since biological raw materials often contain variable quantities of water, water must be first completely separated from the raw material before the raw material is usable for esterification. This increases the costs of the process and reduces the total economy of the manufacture.

In prior art processes, water wash is normally used to remove acid residues from the finished biodiesel; this consumes remarkable quantities of clean, potable water. In addition, removing residues of water from the finished biodiesel consumes a lot of energy.

Publication US 2008/0221344 A1 proposes a process for producing liquid biofuel from bio-based oils and/or fats by transesterification at high pressures and temperatures. In the process, a catalyst can be used for improving the reaction; however, this is not recommended due to a difficult catalyst separation step. This slows down the reaction and makes the process inefficient.

SUMMARY OF THE INVENTION

The present invention provides a process, which is more efficient than prior art processes and does not consume clean water. The process according to the invention for utilizing bio-based oils and/or fats for producing biofuels includes the steps of mixing alcohol with a raw material for forming a reaction mixture, pumping the reaction mixture to a reactor and mixing biogas as a catalyst with the reaction mixture in a selected process step either before or after the supply of the reaction mixture to a high-pressure pump, the biogas includes methane, carbon dioxide and sulfur. The process further includes the steps of adjusting the temperature and pressure of the reactor so that the reaction mixture achieves a supercritical state, esterifying the reaction mixture to produce liquid biofuel, and separating by-products and alcohol from liquid biofuel, wherein methane separated from biogas is recovered after the reactor.

By using supercritical conditions, biofats mixed with water can be used as the raw material in the process without a separate water removal step before the reactor, because, when the reaction mixture is in a supercritical state, any water present is also in a supercritical state. In turn, the use of biogas as a catalyst increases the reaction speed of esterification and improves the yield of finished product from the raw material, the esterification process thus functioning economically and efficiently. In addition, the use of biogas as a catalyst is very economical, since carbon dioxide contained in biogas acts as the catalyst for esterification and methane contained in biogas is separated from carbon dioxide. In this way, carbon dioxide and methane can both be recovered as valuable products. The efficiency of biogas as the catalyst in the process is based on the catalytic effect of carbon dioxide and sulfur contained in biogas. With biogas, a higher esterification degree can be achieved in the esterification process compared to the traditional esterification process, in which a solid or liquid catalyst is used. Methane is conveyed through the reactor in an inert state and methane discharged from the reactor is already at a high pressure and temperature, thus separating easily from biofuel and other components. The pressure of methane discharged from the reactor is close to a pressure that is suitable for transportation.

Preferably biogas also includes sulfur. Sulfur accelerates the esterification reaction and improves the yield. Sulfur contained in biogas functions as a compound with hydrogen, the compound being a reagent ($H_2S$). This hydrogen sulfide precipitates the reactions and raises the extent of esterification (esterification-%). After the esterification process, sulfur and water created in the reaction can be distilled off the end product. Without doubt, hydrogen sulfide may function as a reagent as it decomposes in supercritical conditions and sulfur can be removed from the end product. Hydrogen remains in the end product as a reagent whereas sulfur functions as a catalyst.

In this context, catalyst means biogas or another catalyst added to the reaction mixture in the gaseous state, whereas alcohol acts as a reagent in the process. In this context, by-products mean glycerol, methane, sulfur and carbon dioxide and other possible products, which are not desired among biofuel and are not recirculated.

The portion of biogas in the catalyst may be at least 80% by volume, advantageously at least 90% by volume of the quantity of catalyst used. Thus, the portion of biogas is sufficiently large to accelerate the esterification reaction.

According to an alternative embodiment, 100% by volume of the catalyst is biogas.

Advantageously, the reactor is operated continuously. In this way, a good production capacity can be achieved for the process. At the same time, a continuously operating process is easier to automate than a batch process.

Advantageously, the process uses a reactor in which the reaction mixture has a uniform flow over the entire range of the reactor. This enables a continuous process.

In the process, the temperature of the reactor may range between 70° C. and 500° C., advantageously between 150° C. and 450° C., most advantageously between 250° C. and 330° C. A high temperature enables bringing water to a supercritical state, which also enables using water-containing raw materials.

In the process, the pressure of the reactor may range between 50 and 600 bar, advantageously between 140 and 400 bar, most advantageously between 160 and 260 bar; however, so that alcohol and water possibly contained in the raw material are in a supercritical state. In this way, production of biofuel is possible without a base catalyst. In context of this application, pressure is used to refer to absolute pressure.

As central components, biogas includes methane, carbon dioxide and advantageously also sulfur. Of these, sulfur and carbon dioxide, as catalysts, accelerate the esterification reaction and improve the yield, while methane is conveyed through the reaction space almost in an inert state. More precisely, biogas means gas generating as the result of anaerobic digestion, which may originate from a production plant, a natural source or another similar source.

According to a first embodiment of the process, biogas is fed at a high pressure into a pressurized reaction mixture before the reactor. Since methane does not absorb in the reaction mixture, supplying it to the suction side of the pump would create a cavitation phenomenon, which would prevent or at least deteriorate the pump operation. In other words, biogas is fed to the pressure side of the high-pressure pump.

The supply pressure of biogas may range between 100 and 260 bar. Thus, the pressure corresponds to the pressure of the reaction mixture supplied to the reactor.

According to a second embodiment of the process, biogas is fed into the reaction mixture before the pumping of the reaction mixture. Thus, carbon dioxide contained in biogas is absorbed in the reaction mixture while methane is separated; in this way, methane can be recovered before the pumping of the reaction mixture.

Advantageously, in the second embodiment, biogas and alcohol are fed from the alcohol feed tank to a raw material mixing tank, in which a pressure of 0 to 8 bar and a temperature of −50° C. to 200° C. can be applied. In such conditions, carbon dioxide contained in biogas is well absorbed in the reaction mixture while methane is simultaneously separated.

According to the second embodiment, methane separating from biogas is recovered before the pumping of the reaction mixture, after carbon dioxide has been absorbed in the reaction mixture. Thus, gaseous methane need not be pumped together with the reaction mixture with a pump, which would cause cavitation problems in the pump.

Advantageously, biofuel discharged from the reactor is sprayed to a distillation column. This improves the separation of different fractions, such as carbon dioxide, sulfur and alcohol, from the mixture of biodiesel/glycerol.

According to an embodiment, biofuel is separated from alcohol, sulfur, carbon dioxide, methane and glycerol by distillation. In distillation, the already high temperature of the product flow discharged from the reactor can be utilized, in which case heating is required to a relatively small extent or not at all for vaporizing the various components of the product flow.

Biofuel can also be separated from alcohol and glycerol by centrifugation. The use of a centrifuge is an extremely simple process for separating liquid fractions from each other. Carbon dioxide and sulfur can be separated from the mixture, respectively, by decreasing pressure and by dry washing.

Biofuel can be finally purified by dry washing, wherein biomass is used as the ion exchanger. In this way, it can be ensured that harmful by-products do not remain among biodiesel. Biomass is very advantageous regarding its costs and is a safe ion exchanger for dry washing.

The raw material supplied to the reactor can be pre-heated in the tubular heating section of the reactor before its transfer to the tank-like reaction chamber of the reactor.

The raw material can be processed in the reactor without a base catalyst at such a pressure and temperature at which water contained in the raw material is in a supercritical state. With the pre-processing step, at least the main part of water can be removed from the raw material so that it is possible to use notably smaller amounts of alcohol and catalyst in the main process.

In the reactor, biogas can only be used as a catalyst and alcohol as a reagent. Thus, a portion as large as possible of the reaction volume can be obtained for the use of the reaction mixture and, on the other hand, the finished biofuel is easy to purify when alcohol is the only reagent that needs to be recirculated.

As an alternative to the above, part of the biofuel discharged from the reactor can be recirculated to the reactor as a catalyst. In this case, the space available in the reactor for the reaction mixture is reduced but, on the other hand, biofuel catalyzes the esterification reaction thus accelerating esterification.

The portion of the biofuel discharged from the reactor corresponds to less than 30% by volume, advantageously less than 10% by volume, most advantageously less than 5% by volume of the combined volume of biogas supplied to the reactor and the recirculated biofuel can be recirculated to the reactor to act as a catalyst. Thus, an accelerating effect is achieved for esterification; however, the most part of the reactor volume is still simultaneously used for the esterification of the reaction mixture.

The ratio of biogas supplied may range between 15% and 70%, advantageously between 20% and 50%, relative to the raw material used. Thus, the stoichiometric ratio of carbon dioxide contained in biogas is correct for efficiently catalyzing the reaction.

In the process according to the invention the biogas is used in gaseous form. This is because biogas does not liquefy, even under pressure, in normal circumstances. Biogas is a gas mixture, the main components of which are methane, carbon dioxide and nitrogen. The liquefaction of these gases requires lowering temperature and raising pressure. The following temperatures and pressures are required for liquefaction: i) Carbon dioxide liquefies at temperatures below −57° C. (216 K) at a pressure of 5.812 bar. If the pressure is lower, solid carbon dioxide (dry ice) is formed. ii) If biogas still contains hydrogen sulfide, the biogas liquefies almost at the same temperature as carbon dioxide −60.28° C. (212.87 K) and can be removed from the product. iii) Methane liquefies at temperatures below −162° C. iv) Nitrogen liquefies at temperatures below −195.8° C. (77.35 K) so it remains in its gaseous form. Because biogas is a mixture of different gases, it cannot be liquefied directly, but the different gases of the mixture must be liquefied separately or in stages by removing carbon dioxide first because it liquefies at the highest temperature. Then methane can be liquefied so that nitrogen remains gaseous and is released in the air.

Another object of the invention is to provide a system, which is more efficient than prior art systems and does not consume clean water. The system according to the invention for utilizing bio-based oils and/or fats for producing biofuels includes mixing equipment for mixing alcohol and biogas as a catalyst with a raw material to form a reaction mixture, the biogas including at least methane and carbon dioxide, heating equipment for heating the reaction mixture and a biogas reactor for esterifying the reaction mixture to form biofuel and for local production of biogas. The system further includes a high-pressure pump for pumping the reaction mixture to the reactor, an adjustment equipment for adjusting the temperature and pressure of the reactor to achieve a supercritical state of the reaction mixture for esterification and a first separation equipment for separating by-products and alcohol from biofuel and a second separation equipment for separating methane from the by-products.

A biogas reactor can locally produce biogas functioning as a catalyst in esterification during the esterification process, in which case the separation of biogas generated in the biogas reactor to pure biomethane takes place without specific separation equipment. When using biogas as a catalyst, complex catalyst recovery processes can be avoided, which are needed in prior art processes that use a base catalyst. It should be understood that the separation equipment is also used for separating water, carbon dioxide, methanol and sulfur from biofuel.

Advantageously, the reactor consists of at least one spiral pipe for forming a reaction volume and a heat transfer tank surrounding the pipe for recirculating a heat transfer medium. With such a reactor design, a continuous flow rate is achieved for the reaction mixture thus avoiding separation of glycerol in the middle of the reaction. In addition, a thin spiral pipe can resist very high pressures.

The outer diameter of the spiral pipe may range between 0.5% and 20%, advantageously between 0.5% and 5% of the outer diameter of the heat transfer tank, and the length of the heat transfer tank may be between 1% and 10%, advantageously less than 5% of the length of the spiral pipe. Thus, a sufficient volume remains within the heat transfer tank for the heat transfer effect and flow of the heat transfer medium.

Alternatively, instead of being spiral, the pipe fitted inside the heat transfer tank may be an alternately turning pipe, wherein the alternating sections of the pipe are located at a distance smaller than the pipe diameter from each other. An example of such a shape may be the tortuous path of tubes of a heat exchanger. Alternatively, several spirals may be disposed within each other.

According to an embodiment, the capacity of the reactor can be such that the reactor is fed with 6-10 l/min of reaction mixture to a reactor chamber made of pipe with an inner diameter of 18 mm which reactor chamber has a length of 360 m. Thus, the speed of flow is between 0.4-0.63 m/s and the overall volume of the reactor chamber is 92 l.

The high pressure pump can be arranged to feed the reaction mixture into the reactor at a speed of 0.3 m/s-2.5 m/s, preferably at least at the speed of 0.4-0.7 m/s in order to prevent glycerol from being separated from the reaction mixture. Using the speeds mentioned above the flow of reaction mixture mixes the products of the reaction in the reactor in such way that glycerol cannot separate. The feeding speed must be chosen so that the length of the reaction chamber is long enough that the raw materials of the reaction mixture will react into products.

With a process according to the invention, fats contained in biowaste and wastewater/wastewater sludge can be utilized in an environmentally friendly and energy-efficient manner in the production of biofuel that is suitable for transportation and heating purposes. Advantageously, biofuel is biodiesel, but it can also be kerosene, for instance. Since biodiesel production with this process can be completely carried out without the use of clean water, the process saves global water resources and is particularly suitable for use in biofuel production in areas suffering from clean water scarcity (for example, densely populated Asian countries). In this process, waste fats bound to water can be utilized in biodiesel production that takes place at pressures and temperatures higher than those applied in prior art processes; in other words, it enables a broader raw material base compared to traditional technologies. The use of biogas as a catalyst can be particularly efficient if biogas is locally produced with a biogas reactor during esterification, in which case logistics costs remain minimal. In addition, glycerol can be utilized as a raw material of the biogas plant to produce biogas required as a catalyst.

The combination of methane separation from biogas with the production of liquid biofuel disclosed in the present invention features an advantage since two processes that have traditionally been separate processes with separate equipment can now be combined for the benefit of both processes. During the process, sulfur advantageously is absorbed into alcohol and is separated from methane. At the same time, sulfur increases the reaction rate and yield of the esterification reaction. The pressure of the separated methane recovered from the process is automatically high enough that the methane can be stored in a pumping station for commercial use in biogas vehicles. Therefore, the need for separate methane separation equipment and pressurizing means no longer exists.

Unlike other processes, the process and system according to the invention can be used in continuous operation, which remarkably increases its production potential. An advantage of the use of biogas is also that the base or acid catalyst remaining in biofuel need not be separately separated from it, unlike in prior art processes. In this way, purification of biodiesel to a finished product is easier.

BRIEF DESCRIPTION OF THE DRAWINGS

The invention is described below in detail by referring to the appended drawings, which illustrate some of the embodiments of the invention, in which.

DETAILED DESCRIPTION OF THE INVENTION

Figure 1:
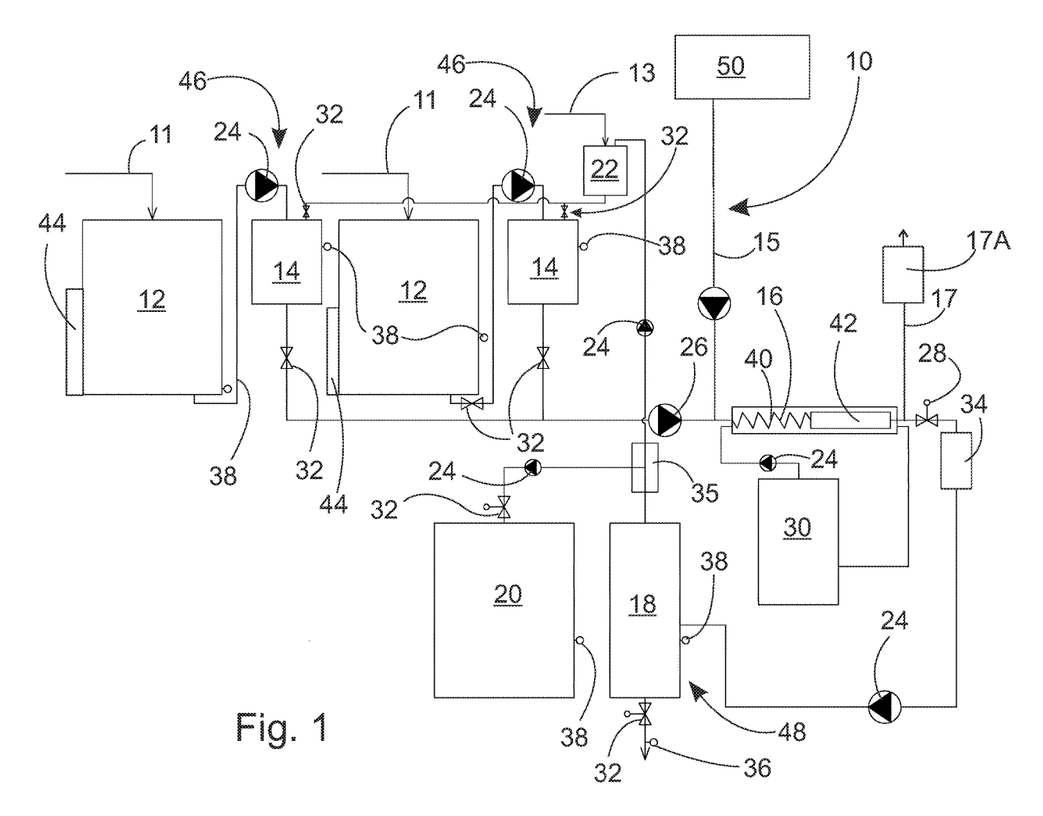
FIG. 1 is a basic process diagram illustrating a first embodiment of the process and system according to the invention for producing biofuel.

FIG. 1 illustrates a first embodiment of the process and system according to the invention. The system according to the invention includes mixing equipment 46 for mixing alcohol 13 with a raw material 11 to form a reaction mixture, heating equipment 44 and 30 for heating the reaction mixture, and a reactor 16 for esterifying the reaction mixture to form biofuel. In addition, the system includes a pump 26 for pumping the reaction mixture to the reactor 16, adjustment equipment for adjusting the temperature and pressure of the reactor 16 in such a way that the reaction mixture is in a supercritical state, and separation equipment 48 for separating biofuel from glycerol, carbon dioxide, sulfur and alcohol. Furthermore, the system includes second separation equipment 17A for separating methane from the liquid biofuel. The above-mentioned structural components are included in all of the embodiments of the equipment meant for the realization of the process and system according to the invention.

The operation of a first embodiment of the process is described below with reference to FIG. 1. The process starts from the supply of a raw material 11 to feed tanks 12. As a raw material of the process, any bio-based fat or oil can be used, for example, used frying fats or vegetable oils, fat and oil fractions generated as industrial side flows, fats from dairy and slaughterhouse biowaste or sludge from fat holding tanks or other similar biowaste fats, which would otherwise constitute environmentally burdening waste. Since fats can be completely solid at the transportation temperature, the raw material is advantageously heated in the feed tank to a temperature of 12° C. to 200° C. with heating equipment 44. For example, the heating equipment 44 may consist of a burner, an electric resistance or equivalent, with which the raw material 11 in the feed tanks 12 can be heated directly or via a heat transfer medium, for example. When adequately heated, all bio-based fats and oils are completely liquid and can then be pumped further in the process. A filter for separating solid impurities from the liquid raw material 11 may be disposed on the bottom of the feed tanks 12.

From the feed tanks 12, the heated liquid raw material is pumped to mixing tanks 14 using a transfer pump 24. Alcohol 13 is fed from a tank of its own to the mixing tanks 14 via a feed tank 22. For example, alcohol used in the reaction may be methanol, ethanol, butanol or isopropanol; thus, alkyl esters, such as methyl esters or ethyl esters, are obtained as the product of esterification. Mixing equipment 46 for mixing together alcohol 13 and the raw material 11 is provided in the vicinity of the mixing tanks 14. For example, the mixing equipment may consist of an agitator, mixer, propeller or similar located within the mixing tank, a pump or a similar mixing device. Advantageously, the number of both the feed tanks 12 and the mixing tanks 14 is at least two, as shown in FIG. 1. Thus, mixing can take place in one tank while simultaneously pumping the raw material mixture further in the process from the other tank that contains raw material already mixed. In this way, it can be ensured that raw material is continuously supplied to the continuously operating esterification reaction. Alternatively, both the heated raw material and alcohol can be mixed together by combining the flows before the high-pressure pump, in which case a separate mixing tank is not needed.

From the mixing tanks 14, the mixture of raw material and alcohol is pumped towards the reactor 16 with the pump 26. Advantageously, the pump 26 is a high-pressure pump, which increases the pressure of the mixture to be pumped to 50-600 bar, advantageously to 140-300 bar, most advantageously to 160-260 bar. To ensure a sufficient supply pressure, the mixing tank 14 must be located above the pump 26, or the supply line must be provided with a transfer pump to ensure that air cannot access the suction line of the high-pressure pump. Advantageously, the high-pressure pump is located as close as possible to the reactor to minimize the dimensions of the transfer piping that is resistant to high pressures. In the first embodiment according to FIG. 1, before sending the reaction mixture to the reactor 16, high-pressure biogas 15 is fed into the reaction mixture with the feed equipment. Biogas 15 can be pressurized with a separate compressor. The pressure of biogas 15 is advantageously equal to or higher than the pressure of the reaction mixture. Carbon dioxide and sulfur contained in biogas are absorbed in alcohol and enable a faster esterification process. Methane is conveyed through the esterification process as an almost inert gas with only 1% to 2% of it absorbing in the product. High-pressure methane 17 can be recovered from the process after the reactor 16. Since the refuelling pressure of biomethane used in transportation purposes is approximately 230 bar, it is worthwhile optimizing the process for this application so that the pressure of methane is sufficiently high without a separate pressure increase, for transportation.

The temperature in the reactor 16 is approximately between 70° C. and 400° C., advantageously between 200° C. and 300° C. and most advantageously between 250° C. and 330° C., and the pressure is between 50 and 600 bar, advantageously between 140 and 400 bar, most advantageously between 160 and 260 bar. The pressure and temperature applied in the reactor are adapted to each other in such a way that the conditions are supercritical for the reaction mixture. Table 1 below shows various combinations of pressure and temperature at which the reaction mixture is in a supercritical state, and shows the effect of temperature on the progress of the esterification reaction.

TABLE 1

Rate of esterification of the raw material relative to the temperature applied in the reactor at 240 bar.

| esterification % | | | | | | | | | | | | | |
|---|---|---|---|---|---|---|---|---|---|---|---|---|---|
| 100 | | | | | | | | | | | | | |
| 95 | | | | | | | | | x | x | x | x | x | x |
| 90 | | | | | | | | x | | | | | x | x |
| 85 | | | | | | | x | | | | | | | |
| 80 | | | | | | x | | | | | | | | |
| 75 | | | | | x | | | | | | | | | |
| 70 | | | | x | | | | | | | | | | |
| 65 | | | x | | | | | | | | | | | |
| 60 | | x | | | | | | | | | | | | |
| 55 | | x | | | | | | | | | | | | |
| 50 | x | | | | | | | | | | | | | |

TABLE 1-continued

Rate of esterification of the raw material relative to the temperature applied in the reactor at 240 bar.

| ester-ification % | | | | | | | | | | | | | | | | | | | | |
|---|---|---|---|---|---|---|---|---|---|---|---|---|---|---|---|---|---|---|---|---|
| 45 | | | x | | | | | | | | | | | | | | | | | |
| 40 | | x | | | | | | | | | | | | | | | | | | |
| 35 | x | | | | | | | | | | | | | | | | | | | |
| 30 | | | | | | | | | | | | | | | | | | | | |
| 25 | | | | | | | | | | | | | | | | | | | | |
| 20 | | | | | | | | | | | | | | | | | | | | |
| 15 | | | | | | | | | | | | | | | | | | | | |
| 10 | | | | | | | | | | | | | | | | | | | | |
| 150 | 160 | 170 | 180 | 190 | 200 | 210 | 220 | 230 | 240 | 250 | 260 | 270 | 280 | 290 | 300 | 310 | 320 | 330 | 340 | 350 |
| | | | | | | | | | Temperature ° C. | | | | | | | | | | | |
| | 35 | 40 | 45 | 50 | 55 | 60 | 65 | 70 | 75 | 80 | 85 | 90 | 95 | 97 | 97 | 97 | 95 | 93 | 91 | 89 |

The conditions of the reactor should be kept as close as possible to the minimum temperature and pressure at which the reaction mixture is in a supercritical state to avoid igniting trichromium dioxide and acroleine contained in the raw material. Combustion of these components produces a detrimental color and smell for biofuel, simultaneously generating toxic gas compounds. On the other hand, combustion changes the reaction to an exothermic reaction, which reduces heating costs.

At the same time, the conditions are also supercritical regarding water possibly contained in the raw material. The esterification reaction converts the reaction mixture to biofuel and by-products in accordance with the following reaction equations:

$$RCOOCH_2 \qquad\qquad CH_2OH$$
$$RCOOCH_2 + 3CH_3OH + \text{biogas} \rightarrow 3R\text{-}COOCH_3 + CH_2OH + CH_4$$
$$RCOOCH_2 \qquad\qquad CH_2OH$$

More precisely, biofuel is advantageously biodiesel, which is mainly composed of C9 to C25 hydrocarbons. Biodiesel contains paraffins and naftenes approximately 65% to 95%, aromatic hydrocarbons 5% to 30% and olefins 10% at the maximum of the total volume. Biofuel can also be kerosene, for example.

Advantageously, the system 10 includes a heating tank 30, in which a heat transfer medium is heated before feeding it to the reactor 16. The heat transfer medium is advantageously a liquid, but it can also be steam or flue gas. The heat transfer medium advantageously circulates in a closed circuit and is thus sent back to the heating tank 30 when discharged from the reactor 16. Advantageously, heat can also be transferred to the heat transfer medium from the distillation column functioning as the separation tank, utilizing the heat of condensation of the distillation column for heating the heat transfer medium.

Figure 2:
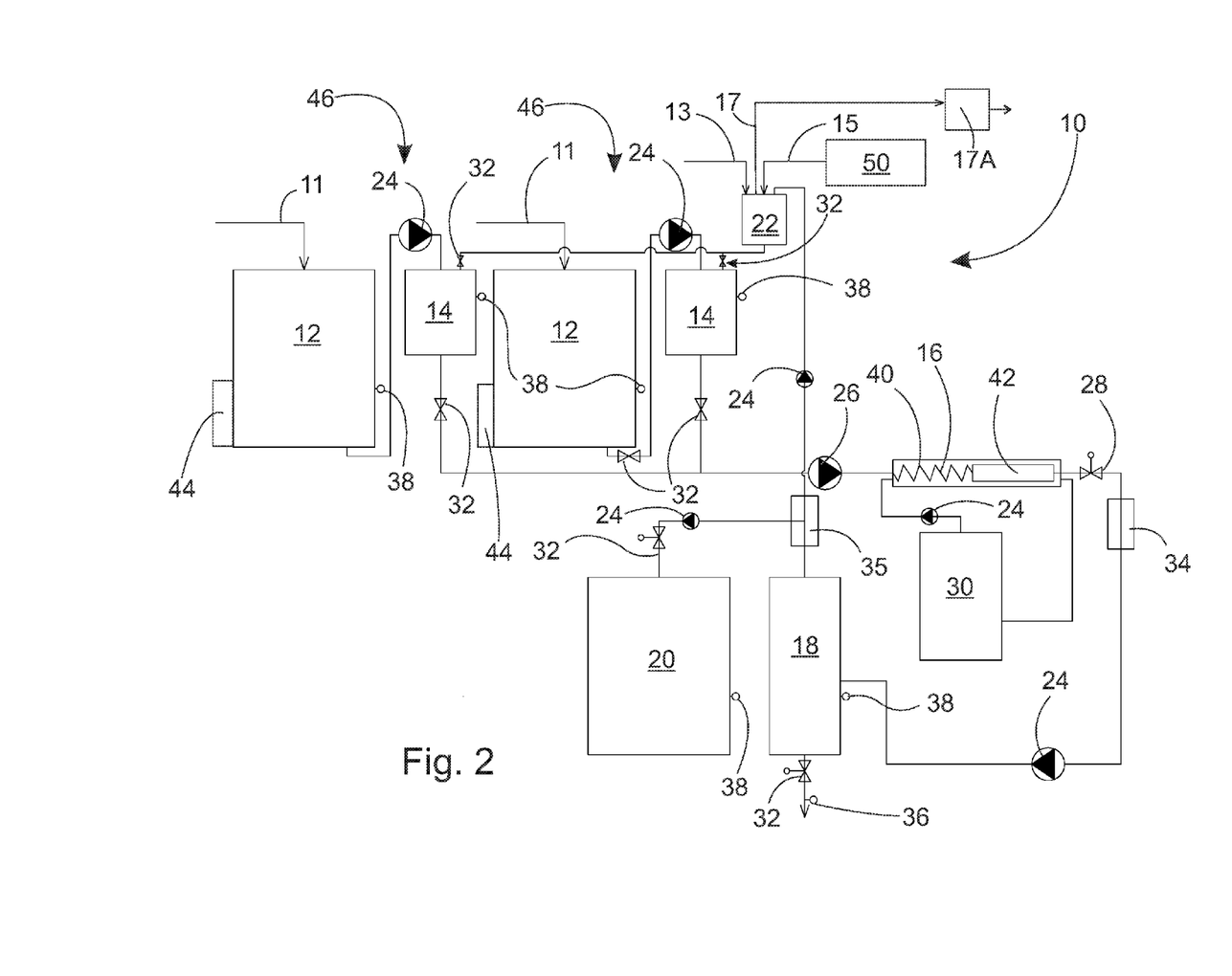
FIG. 2 is a basic process diagram illustrating a second embodiment of the process and system according to the invention for producing biofuel.
Figure 3:
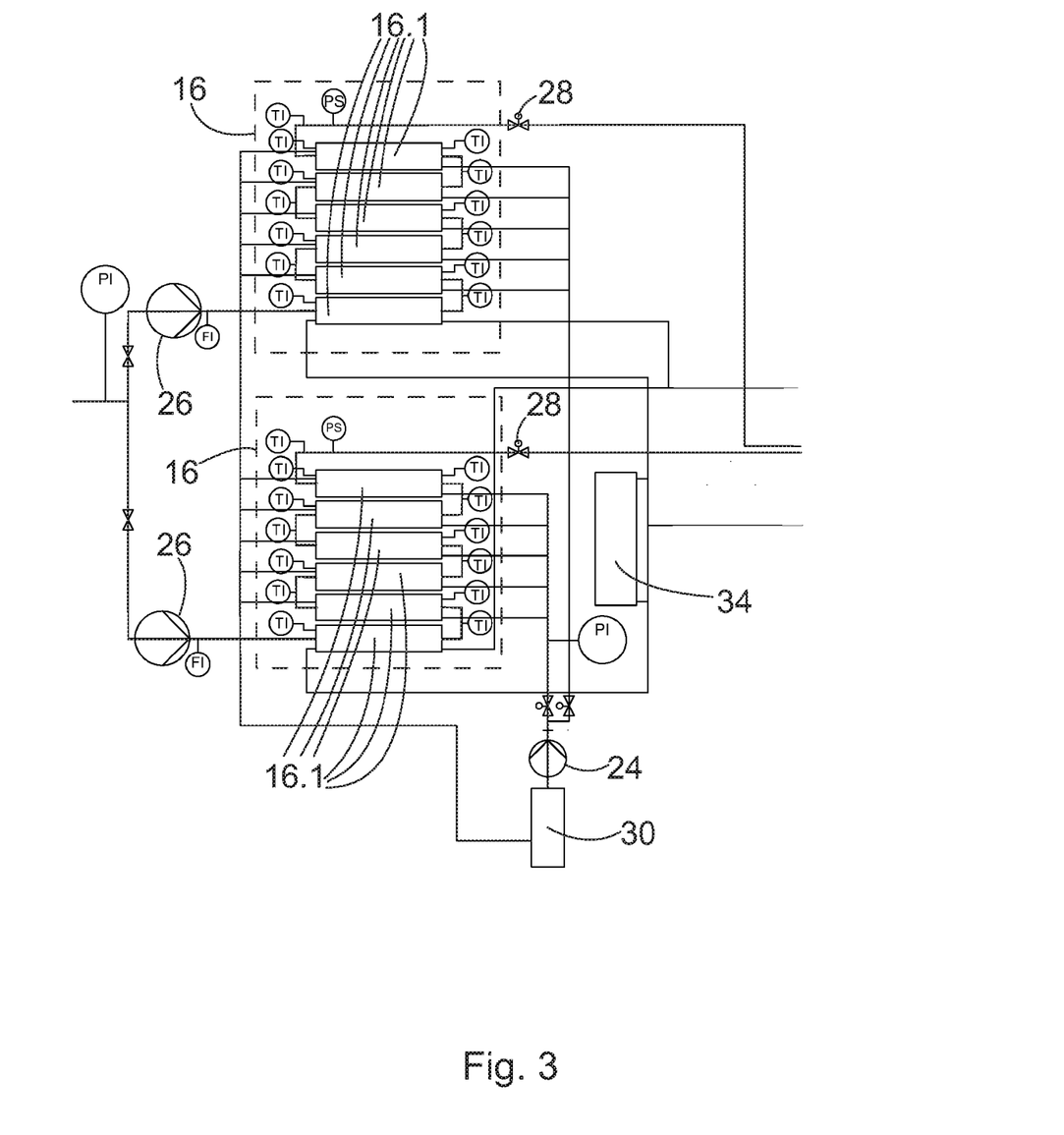
FIG. 3 is a more detailed view of a reactor design according to an embodiment of the system according to the invention.

FIG. 3 shows an advantageous design of a reactor, deviating from the reactor of FIGS. 1 and 2, wherein the reactor has several, advantageously between four and eight, more advantageously six heat transfer tanks 16.1 connected in series. Advantageously, the process has at least two such entities consisting of six heat transfer tanks disposed in parallel to provide a sufficient capacity. With such equipment, an adequate dwelling time in the reactor is achieved for the reaction mixture, for sufficiently complete esterification.

Figure 4A:
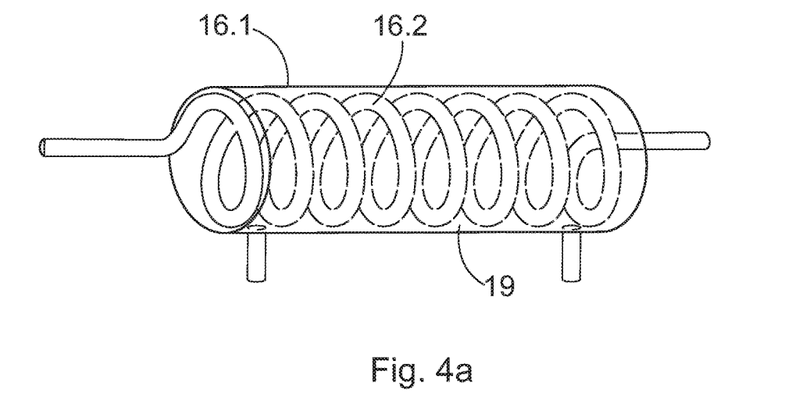
FIG. 4a is a more detailed basic diagram of the design of an individual heat transfer tank of the reactor of FIG. 3.

In turn, FIG. 4a shows the design of an individual heat transfer tank 16.1 in more detail. Advantageously, the reactor is composed of six successive linear heat transfer tanks 16.1, of which each can have a diameter of 210 mm. The heat transfer tank can also deviate from the linear form, being spherical, for example. Within each heat transfer tank 16.1, approximately 60 meters of pipe 16.2 with an external diameter of 20 mm and a possible wall thickness of 2 mm is advantageously disposed. To achieve a larger reaction volume and surface area, the pipe 16.2 is a construction twisted to a round or an angled spiral form, which is heated from the outside with a heat transfer medium. Such a pipe is particularly resistant to high pressures. Within each heat transfer tank 16.1, a heat transfer medium 19, which is pumped from the heating tank 30 of FIGS. 1 and 2, flows at the center of and around the spiral of the spiral pipe 16.2. The heat transfer medium is advantageously heat transfer oil. The first and partly also the second heat transfer tank of the six successive linear heat transfer tanks act to preheat the reaction mixture, over the length of which, the temperature of the reaction mixture increases to such a value that the reaction mixture is supercritical at the pressure applied. The other four linear heat transfer tanks function as the actual reaction space in which esterification takes place in the supercritical conditions of the reaction mixture.

By advantageously submerging the spiral pipe in a heat transfer medium, it is possible to achieve efficient heat transfer from the heat transfer medium to the reaction mixture inside the pipe. In this way, the reaction mixture is heated to the required reaction temperature. The heat transfer medium, such as heat transfer oil, can be heated using electrical resistances, for instance, or the heat transfer oil can also be heated using the exhaust gas heat exchanger of a CHP (Combined Heat and Power) unit, which can heat the heat transfer oil to a temperature exceeding 400° C. Another advantage of a pipe set as a spiral is its remarkably low production cost compared to an individual reaction chamber, which would correspond to the volume of a spiral pipe in terms of volume. With a spiral pipe, a uniformly progressing flow is achieved for the reaction mixture in the piping so that glycerol generated as the result of the esterification reaction cannot separate from biofuel in any position, causing obstructions in the reactor.

Figure 4B:
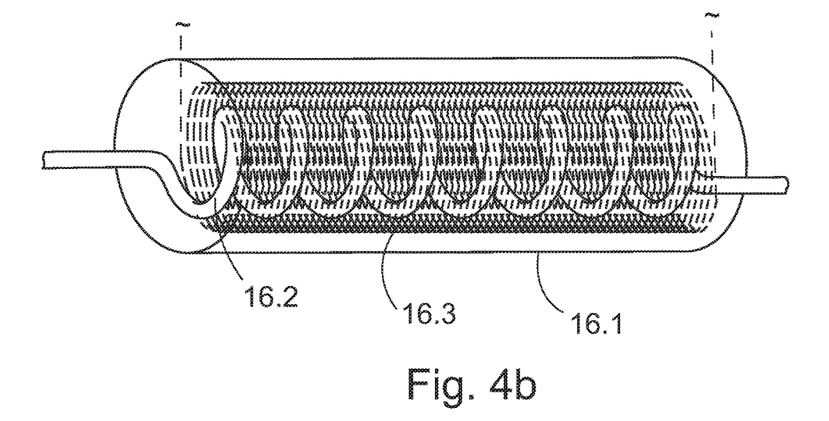
FIG. 4b is a second embodiment of the reactor.

FIG. 4b shows a second embodiment of the reactor used in the system according to the invention which differs from the embodiment of FIG. 4a in terms of its heating means. In the embodiment of FIG. 4b, the heating of the reaction mixture takes place by heating the pipe 16.2 with the aid of induction coils 16.3 which form the heating means. The induction coils 16.3 are situated around the pipe 16.2 and an alternating current led into the induction coils generates an alternating magnetic field inside the induction coils, which induces circulating currents inside the induction coils 16.3 which heat the structure of the pipe 16.2. Preferably the pipe is made of black iron with an especially high resistance, so that it heats up especially efficiently due to electricity. For example, with a reactor having 60 m of pipe set on a spiral the power of the induction coils can be about 200-500 kW. In this embodiment, the reactor is also preferably insulated from the environment by a tank 16.1. In this case the tank is heat insulated, but also prevents the magnetic field from getting outside the reactor.

Figure 4C:
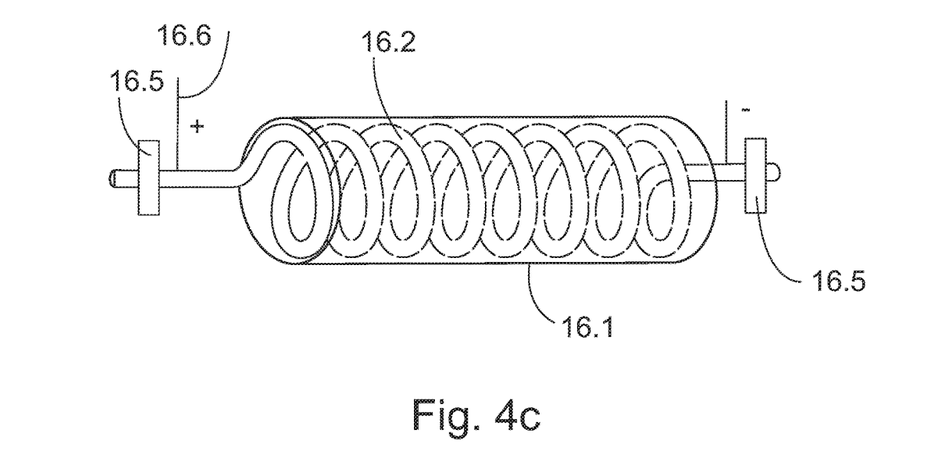
FIG. 4c is a third embodiment of the reactor.

FIG. 4c shows a third embodiment of the reactor used in the system according to the invention which differs from the embodiment of FIG. 4a in terms of its heating means. In the embodiment of FIG. 4c, the heating of the reaction mixture takes place by heating the pipe 16.2 with the aid of electric resistors 16.4 which form the heating means. The electric resistors 16.4 can be situated at both ends of the pipe 16.2. The pipe 16.2 is preferably made of metal, which conducts electricity. An insulating stop 16.5 is formed on the pipe 16.2, the stop preventing electric current from getting conducted outside the reactor structure. For example, with a reactor having 60 m of pipe set on a spiral the power of the electric resistances can be about 200-500 kW. In this embodiment, the reactor is also preferably insulated from the environment by a tank 16.1. In this case, the tank is thermally and electrically insulated. Alternatively, the pipe itself can be used as an electric resistance.

Figure 5:
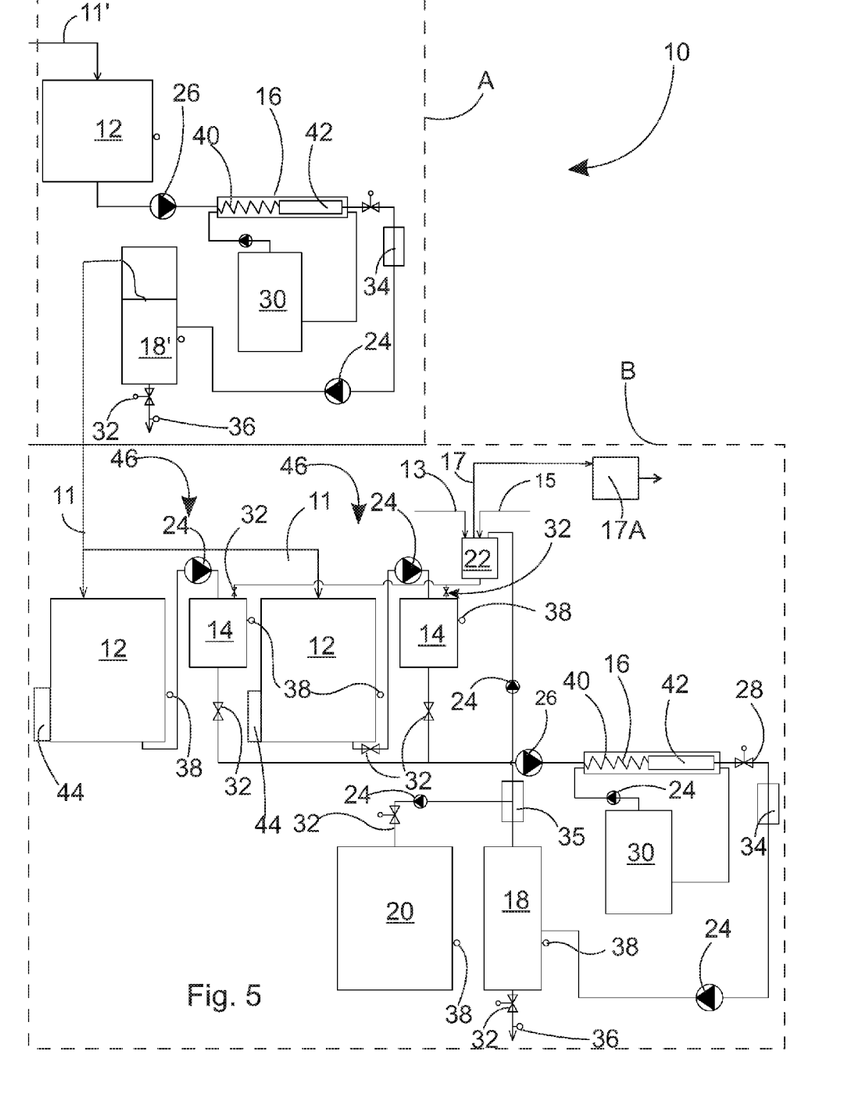
FIG. 5 is a basic process diagram illustrating a third embodiment of the process and system according to the invention for producing biofuel.

Alternatively, the reactor may also include two parts according to FIGS. 1, 2 and 5, namely the tubular heating section 40 and the tank-like reaction chamber 42. Alternatively, both of these can function as a reactor even on their own. However, a problem with a tank-like reaction chamber is the tendency of glycerol to separate from biofuel, unless mixing equipment is provided within the tank-like reactor. The reaction chamber can also be a bottle-like reactor, for example, which can be submerged in the heat transfer medium.

When using biogas, the esterification reaction can be notably faster than a prior art esterification reaction, which takes place at low pressures and temperatures. In the process according to the invention, the esterification reaction can take place in 2 to 20 minutes, advantageously in 8 to 12 minutes, depending on the temperature, pressure, mixing and the composition of the raw material. In prior art esterification, the dwelling time has been approximately two hours. The composition of the raw material and/or alcohol selected may also slightly influence the ratios of the components of the product flow and the required process conditions. During the esterification reaction, the product flow also receives some water, which is completely sterile due to the supercritical conditions of the reactor, and so are the other end and side products. In addition, the use of biogas improves the yield by changing the pH of the mixture and by weakening the glycerol bond between triglycerides. Advantageously, biogas is a combination of methane, carbon dioxide and sulfur ($CH_4 + CO_2 + S$).

According to FIGS. 1 and 2, the biofuel and side products produced are discharged from the reactor 16 via the pressure reducing valve 28 and the heat exchanger 34 to the separation tank 18. More precisely, after the reactor, the mixture is led out from the reaction chamber via a high-pressure pipe. If necessary, the mixture is heated or cooled with the heat exchanger before sending it to the pressure reducing valve. The heat exchanger 34 adjusts the temperature of the product flow to between 210° C. and 340° C., depending on the reaction speed and pressure of the reactor. If the temperature of the product flow discharged from the reactor is lower than this, then the product flow is heated and if higher then cooled. Any heat recovered can be utilized, for example, for heating the heating tank of the heat transfer medium.

From the pressure reducing valve, the mixture is sent at a pressure of 1 to 100 bar to a nozzle, which sprays the atomized mixture to a distillation column, advantageously functioning as the separation tank. With this, separation of alcohol from the mixture can be accelerated. A vacuum can also be utilized for separating alcohol from the mixture. In the embodiment of FIG. 1, the separation tank 18 is a distillation column, the temperature of which can be adjusted between 70° C. and 350° C., at which temperatures alcohol and biofuel are vaporized. Liquid glycerol is recovered as the bottoms product and biofuel and alcohol are collected as the overhead product. The overhead product is condensed to a liquid at the different heights, i.e. at different temperatures, of a high distillation column. At normal pressures, the temperatures range between 210° C. and 250° C., for example. The liquid can also be collected from the different stages of the distillation column, in which case it can be fractioned in accordance with the hydrocarbon composition. The fractions collected from different stages have slightly different properties; for example, shorter hydrocarbon chains have a lower cloud point, whereas hydrocarbons with longer chains have a higher specific heat capacity. Liquid biofuel can be pumped to the biofuel storage tank 20 via the shutoff valve 32 using the transfer pump 24. Liquefied alcohol can be transferred back to the alcohol feed tank 22 with the transfer pump 24. In this way, alcohol is recirculated in the process in a closed circuit; thus, 20% to 50% of alcohol only needs to be added. Alternatively, the biofuel/glycerol mixture can be removed from the distillation column as the bottoms product, after which glycerol is separated from biofuel based on gravitation, for example.

Glycerol removed from the separation tank 18 as the bottoms product can be distinguished from the product flow that is continuously pumped into the separation tank using a color identifier 36, for example, based on the color. Glycerol is removed as the bottoms product via the shutoff valve 32. Glycerol can be transferred for further processing where it can be used, for example, as raw material in the production of soaps in the chemical industry or as raw material in the production of biogas in bioenergy production. In the process according to the invention, the equipment 10 may include level gauges 38 associated with all of the tanks for monitoring tank levels.

FIG. 2 illustrates a second embodiment of the process according to the invention. The equipment 10 of FIG. 2 deviates from the equipment according to the first embodiment shown in FIG. 1 regarding the supply point of biogas used and the recovery of methane. In the embodiment of FIG. 2, biogas and alcohol are fed from the alcohol feed tank 22 to the raw material mixing tank 14, wherein, in this case, a pressure of 2 to 8 bar is applied in addition to a temperature of −50° C. to 200° C. Biogas is absorbed in the reaction mixture for the part of carbon dioxide, and methane is separated from biogas. Methane can be recovered from the alcohol feed tank 22 according to FIG. 2 before the pumping of the reaction mixture with the high-pressure pump, in which gaseous methane would cause pump cavitation. This can be performed by alternating between the mixing of catalyst and the recovery of methane. If necessary, methane is processed further, for example, by drying, before its use. The high-pressure reaction mixture is supplied to the reactor.

To be used, methane utilized for transportation purposes must be purified (i.e. by increasing its methane content and removing impurities) and pressurized to so-called biomethane, which corresponds to natural gas with regards to its composition and properties. This is generally performed using biogas processing equipment specifically designed for the purpose, the investment and operation costs of which are relatively high. In the process described in this application, purified and pressurized biogas, i.e. biomethane, is achieved as a side product with low production costs; this is directly suitable for transportation purposes or, for example, to be supplied to a natural gas network, or transported to other applications via a gas network.

In the process according to the invention, alcohol can be used in a volume ratio of approximately 15% to 25% (according to the molecular weight) compared to the raw material supplied. Biogas is used, in turn, in a volume ratio of 15% to 70% (according to the molecular weight) compared to the raw material supplied. During the esterification reaction, approximately 70% to 90% of methyl or ethyl ester, 10% to 30% of glycerol and 12% to 30% of methane is produced.

Although the separation tank 19 is a distillation column in the embodiments of FIGS. 1 and 2, it should be understood that other means could also be used in the process for separating glycerol, alcohol and finished biofuel from each other. One such means is to carry out separation with a settling tank, located after the heat exchanger following the reactor, in which glycerol is separated from alcohol and biofuel by settling. After this, alcohol is separated from the biofuel in a separate buffer tank by vaporizing alcohol. Biofuel remaining in the buffer tank and any impurities contained in it are pumped to a dry wash column, which is filled with biomass functioning as the ion exchanger, a mixture of saw cuttings, saw dust and/or peat for example. Magnesium silicate can also be added to biomass, or it can be added to unwashed biodiesel before pumping it to a biomass filter. Magnesium silicate binds impurities from biofuel, which are removed during the filtering of biomass. Advantageously, biomass is automatically supplied with a screw feeder, for example, from the filter pulp tank to the top section of the dry wash column and is removed from its bottom section to the tank of the used filter pulp. Used filter pulp can be compressed to recover biofuel attached to it. For example, used biomass can be pelletized or briquetted or utilized as a fuel in heat production, for instance.

FIG. 5 shows a third embodiment of the process according to the invention. Such an embodiment is suitable for use in particular for the processing of raw materials with a significant water content, exceeding 30%. Since the quantity of alcohol and catalyst required in the process is directly proportional to the quantity of water contained in the raw material, the consumption of alcohol and catalyst is high when the raw material contains a lot of water. Since the consumption of these has a significant impact in terms of the total economy of the process, the raw material can be pre-processed in accordance with FIG. 3. In this embodiment, the raw material can be first pre-processed in the pre-processing step A to form bio-oil, which is then used as the raw material in the main process B, which can be, for example, a similar process as the one according to the second embodiment of FIG. 2.

In practice, the pre-processing step A can be otherwise similar to the main process with the exception that during the pre-processing, the raw material is processed in the reactor without catalyst at a pressure and temperature at which the water contained in the raw material is in a supercritical state. Thus, part of the raw material is esterified and the rest is separated as bio-oil, which can be separated from glycerol in a way similar to the separation of glycerol in the main process. With the pre-processing step, at least the main part of water can be removed from the raw material so that it is possible to use notably smaller amounts of alcohol as a reagent and biogas as a catalyst in the main process. Alternatively, the main process can also be used without separate pre-processing in such a way that the reactor is operated according to the batch operation principle using recirculation. In this case, the raw material is first conveyed through the reactor without alcohol and catalyst and recirculated to the feed tank, after which alcohol and catalyst are mixed with the raw material and the reaction mixture is esterified in supercritical conditions, as explained in the process descriptions given above, to form biofuel.

According to a fourth embodiment, biodiesel can be separated from other side products by centrifugation. During centrifugation, different materials are separated from each other based on their specific weights.

In the process according to the invention, the process equipment used, excluding the reactor, can be completely conventional prior art equipment. The process is scalable from production plants with an annual capacity of a few tons to production capacities of tens of millions of tons.

In the figures, the various components of the process equipment are referred to using the following reference numbers:

10 system
11 raw material
11' bio-oil
12 feed tank
13 alcohol
14 mixing tank
15 biogas
16 reactor
16.1 heat transfer tank
16.2 spiral pipe
16.3 induction coil
16.4 electric resistor
16.5 electric insulation
17 methane
17A second separation equipment
18 separation tank
19 heat transfer medium
20 biofuel storage tank
22 alcohol feed tank
24 transfer pump
26 high-pressure pump
28 pressure reducing valve
30 heating tank for the heat transfer medium
32 shut-off valve
34 heat exchanger
35 second heat exchanger
36 color detector
38 level gauge
40 tubular heating section
42 reaction chamber
44 heating equipment
46 mixing equipment
48 separation equipment

The invention claimed is:

1. A process for utilizing bio-based oils and/or fats for producing biofuels using a reactor having at least one spiral pipe and a heat transfer tank surrounding said pipe, comprising the steps of:
mixing alcohol with a raw material for forming a reaction mixture,
pumping the reaction mixture to the reactor,
mixing biogas as a catalyst with the reaction mixture in a selected process step either before or after the supply of the reaction mixture to a high-pressure pump, the biogas including methane and carbon dioxide and further including sulfur functioning as a catalyst for an esterification process,
adjusting a temperature and pressure of the reactor so that the reaction mixture achieves a supercritical state,
esterifying the reaction mixture to produce liquid biofuel and by-products,
separating the by-products including methane and alcohol from the liquid biofuel, and
recovering separated methane.

2. A process according to claim 1, wherein said sulfur is in the form of hydrogen sulfide, said sulfur precipitating reactions and raising an extent of esterification.

3. A process according to claim 1, wherein the step of mixing the biogas with the reaction mixture includes supplying the biogas under a high pressure into the pressurized reaction mixture before the reactor.

4. A process according to claim 1, wherein the step of mixing the biogas with the reaction mixture includes feeding the biogas into the reaction mixture before the pumping of the reaction mixture.

5. A process according to claim 3, wherein the step of recovering separated methane includes recovering methane separated from the biogas before the pumping of the reaction mixture and after carbon dioxide has been absorbed in the reaction mixture.

6. A process according to claim 1, including the step of using the reactor in continuous operation.

7. A process according to claim 1, wherein the temperature of the reactor ranges between 70° C. and 500° C.

8. A process according to claim 1, wherein the temperature of the reactor ranges between 150° C. and 450° C.

9. A process according to claim 1, wherein the temperature of the reactor ranges between 250° C. and 330° C.

10. A process according to claim 1, wherein the pressure of the reactor ranges between 50 and 600 bar.

11. A process according to claim 1, wherein the pressure of the reactor ranges between 140 and 400 bar.

12. A process according to claim 1, wherein the pressure of the reactor ranges between 160 and 260 bar.

13. A process according to claim 1, wherein the step of separating biofuel from alcohol and by-products is performed by distillation.

14. A process according of claim 1, including the step of purifying biofuel by dry washing, wherein biomass is used as an ion exchanger.

15. A process according to claim 1, wherein the reaction mixture has a uniform flow over an entire range of the reactor.

16. A process according to claim 1, wherein the biogas is only used as the catalyst and alcohol as a reagent in the reactor.

17. A process according to claim 1, including the step of recirculating part of the biofuel discharged from the reactor back to the reactor to act as a catalyst.

18. A process according to claim 17, wherein the portion of the biofuel discharged from the reactor corresponds to less than 30% by volume of a combined volume of the biogas supplied to the reactor.

19. A process according to claim 17, wherein the portion of the biofuel discharged from the reactor corresponds to less than 10% by volume of a combined volume of the biogas supplied to the reactor.

20. A process according to claim 17, wherein the portion of the biofuel discharged from the reactor corresponds to less than 5% by volume of a combined volume of the biogas supplied to the reactor.

21. A process according to claim 1, wherein a ratio of the biogas supplied ranges between 15% and 70% relative to the raw material used.

22. A process according to claim 1, wherein a ratio of the biogas supplied ranges between 30% and 45% relative to the raw material used.

* * * * *